United States Patent [19]
Kuntz et al.

[11] Patent Number: 4,628,122
[45] Date of Patent: Dec. 9, 1986

[54] PROCESS FOR CONCENTRATING AND RECOVERING CHLORAL

[75] Inventors: Frederick J. Kuntz, Lake Charles, La.; Henry W. Schussler, North Canton, Ohio

[73] Assignee: PPG Industries, Inc., Pittsburgh, Pa.

[21] Appl. No.: 793,876

[22] Filed: Nov. 1, 1985

[51] Int. Cl.$^4$ .............................................. C07C 45/80
[52] U.S. Cl. ................................... 568/492; 568/449; 568/495
[58] Field of Search ........................ 568/492, 495, 449

[56] References Cited

U.S. PATENT DOCUMENTS

| | | | |
|---|---|---|---|
| 2,584,036 | 1/1952 | Mahoney et al. | 202/42 |
| 2,746,912 | 5/1956 | Park et al. | 202/42 |
| 3,055,955 | 9/1962 | Hodges | 260/656 |
| 3,140,244 | 7/1964 | Simek et al. | 202/46 |
| 3,378,597 | 4/1968 | Dehn et al. | 260/652 |
| 3,427,359 | 2/1969 | Rectenwald et al. | 260/659 |
| 3,488,398 | 1/1970 | Harpring et al. | 260/659 |
| 3,679,373 | 7/1972 | Vancamp et al. | 23/288 L |
| 3,996,300 | 12/1976 | Ahlstrom | 260/652 P |
| 4,028,427 | 6/1977 | Tsao | 260/659 R |
| 4,263,269 | 4/1981 | Little et al. | 568/495 |
| 4,513,152 | 4/1985 | Schillawski | 568/492 |

FOREIGN PATENT DOCUMENTS 1129942  5/1962  Fed. Rep. of Germany .
 843996  8/1960  United Kingdom .

OTHER PUBLICATIONS

L. F. Albright, "Manufacture of Vinyl Chloride", *Chemical Engineering*, Apr. 10, 1967, pp. 219–224 and 226.
R. W. McPherson, C. M. Starks, and G. J. Fryar, "Vinyl Chloride Monomer . . . What You Should Know", *Hydrocarbon Processing*, Mar. 1979, pp. 75–88.

*Primary Examiner*—Werren B. Lone
*Attorney, Agent, or Firm*—George D. Morris

[57] ABSTRACT

Chloral is removed from aqueous hydrochloric acid containing chloral in a stripping zone at superatmospheric pressure and concentrated in a rectifying zone at superatmospheric pressure. The method is particularly suited for the treatment of feed compositions originating from the oxychlorination of ethylene.

22 Claims, 1 Drawing Figure

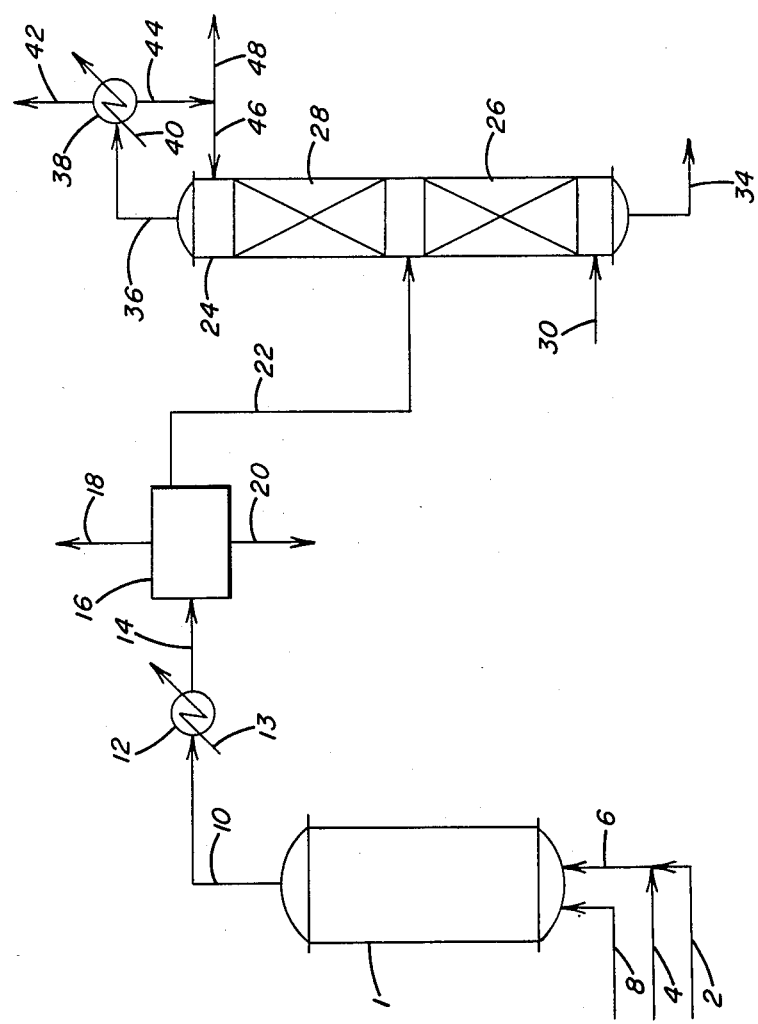

PROCESS FOR CONCENTRATING AND RECOVERING CHLORAL 1,2-Dichloroethane is frequently produced in a reactor system from which at least one stream of crude 1,2-dichloroethane comprising contaminating amounts of various impurities including chloral hydrate. Typical sources of such crude 1,2-dichloroethane include processes in which ethylene is oxychlorinated in packed bed, fluidized bed, or liquid phase reactors and processes in which ethane is oxychlorinated. See, for example, L. F. Albright, "Manufacture of Vinyl Chloride", *Chemical Engineering*, April 10, 1967, pages 219–224 and 226, R. W. McPherson, C. M. Starks, and G. J. Fryar, "Vinyl Chloride Monomer... What You Should Know," *Hydrocarbon Processing*, March 1979, pages 75–88, and U.S. Pat. Nos. 3,055,955; 3,427,359; and 3,679,373, the entire disclosures of which are incorporated herein by reference, directed to oxychlorination.

Using the oxychlorination of ethylene as an example, ethylene, hydrogen chloride, and an oxygen-containing gas (usually commercial oxygen, air, or oxygen-enriched air) are reacted to form a gas stream which is removed from the reactor and condensed to form two liquid phases, one organic and the other aqueous. The liquid aqueous phase is substantially separated from the liquid organic phase and is usually treated with base, such as alkali metal hydroxide, to decompose the chloral which it contains. The treatment with base unfortunately also converts the hydrochloric acid to a salt, thereby resulting in loss of the hydrochloric acid.

The problem of recovering aqueous hydrochloric acid which is substantially free of organic contaminants (including chloral) from aqueous hydrochloric acid containing such contaminants, was addressed in U.S. Pat. No. 4,263,269, the disclosure of which, in its entirety, is incorporated herein by reference. In the process described in that patent, the contaminated aqueous hydrochloric acid is stripped countercurrently under superatmospheric pressure to provide a purified hydrochloric acid solution containing substantially reduced amounts of such organic contaminants.

The process of U.S. Pat. No. 4,263,269 can be used to satisfactorily produce purified hydrochloric solutions, but the overhead poses a disposal problem due to its chloral content.

It is often desired to dispose of chloral by incineration. However, when the chloral is in the form of a dilute aqueous solution, incineration is often economically infeasible, primarily for two reasons. First, in order to dispose of a given amount of chloral in a given period of time, large volumes of the dilute solution must be introduced to the incineration during that time period and the incineration facility must be physically large enough to accommodate the large volumes of materials flowing through the system. Second, although chloral itself has fuel value, when the chloral is in the form of a dilute aqueous solution, the heat required to raise the solution to incineration temperatures (typically on the order of about 1100° C.) is quite large, primarily because of the large volume of water that must be heated. This requires large amounts of additional fuel and is unduly expensive and wasteful of resources.

As the concentration of chloral in the aqueous solution introduced to the incineration process is increased, both the volumetric rate of solution introduction and the amount of additional fuel required are reduced. In a large chloroorganics plant where chloral is produced as a byproduct from the oxychlorination of ethylene using hydrogen chloride and an oxygen-containing gas, incineration can become an economically viable option for waste disposal of the chloral when the chloral concentration in the solution introduced to the incineration process is at least about 30 percent by weight. As the chloral concentration is increased above the viability point, the operating costs and fuel requirements of the incineration facility are further reduced. At some point (very roughly about 65 percent chloral by weight), which depends upon the operating parameters of the particular incineration process employed, taken as a whole, the chloral concentration is great enough that the solution is a net producer, rather than a net consumer, of heat. The heat so produced may be used in a variety of ways, including the production of steam.

It will be recognized that the above discussion is also applicable to aqueous chloral solutions containing contaminants in addition to chloral, although precise numerical values may change. The magnitude and direction of the change will depend upon the identities, heat capacities, heats of combustion, and concentrations of the additional contaminants.

In some instances it is desirable to process dilute aqueous chloral solutions to produce aqueous solutions of increased chloral content for purposes other than incineration. Such more concentrated aqueous chloral solutions, for example, may be introduced to reactions where the chloral is a reactant, or they may be introduced to other processes where the chloral is further purified.

The present invention, which is an improvement to the stripping process of U.S. Pat. No. 4,263,269, permits separation of an aqueous hydrochloric acid solution contaminated with a moderate amount of chloral into an aqueous hydrochloric acid composition having a low concentration of chloral and a chloral-rich composition having a higher chloral concentration than is obtained by practice of the stripping process alone. Accordingly, in the method wherein: (a) a feed composition comprising both aqueous hydrochloric acid and from about 1 to about 12 percent by weight chloral is introduced to a stripping zone; (b) aqueous hydrochloric acid containing chloral is countercurrently contacted in the stripping zone with steam or reboiled aqueous acid vapors under superatmospheric pressure conditions to produce a purified, aqueous hydrochloric acid solution having a lower concentration of chloral than the feed composition; and (c) at least a portion of the solution is recovered, the invention is the improvement comprising: (d) introducing liquid reflux to a rectifying zone at a reflux ratio of from about 0.4:1 to about 15:1, the liquid reflux comprising water and chloral in which the chloral concentration is in the range of from about 30 to about 89 percent by weight; (e) countercurrently contacting in the rectifying zone under superatmospheric pressure conditions, vapors comprising hydrochloric acid vapor and chloral vapor with descending liquid comprising chloral and water; and (f) recovering a product comprising chloral and water in which the chloral concentration is in the range of from about 30 to about 89 percent by weight.

As used throughout the present specification and claims, the reflux ratio is the mass flow rate of the liquid reflux divided by the mass flow rate of the chloral-rich product which is recovered.

The usual method for analyzing aqueous solutions of chloral and aqueous hydrochloric acid solutions containing chloral is gas chromatography. This method does not distinguish between anhydrous chloral and chloral hydrate, and the quantitative value of chloral determined includes both the anhydrous chloral and the chloral hydrate expressed on an anhydrous basis. As used throughout the present specification and claims, the term "chloral" means chloral expressed on an anhydrous basis, irrespective of whether the chloral is hydrated or not, unless the term is either expressly or contextually qualified otherwise.

For a better understanding of the invention, reference may be made to the drawing which shows diagrammatically an embodiment of the invention.

The particular form of apparatus used in practicing the invention may vary widely. Usually, but not necessarily, the rectifying zone and the stripping zone are contained in the same distillation column in which vapor from the top of the stripping zone is allowed to pass upward into the rectifying zone and liquid from the bottom of the rectifying zone is allowed to pass downward into the top of the stripping zone. Examples of various columns that may be used include bubble cap columns, sieve plate columns, packed columns, and similar devices. In all cases the feed point is considered to be a part of the stripping zone.

The feed composition comprises from about 1 to about 12 percent by weight chloral. In many cases the chloral concentration is in the range of from about 3 to about 12 percent by weight. Often it is in the range of from about 3 to about 10 percent by weight. A chloral concentration in the range of from about 4 to about 6 percent by weight is preferred.

The concentration of hydrochloric acid, taken as HCl, present in the feed composition may vary widely. Ordinarily the hydrochloric acid concentration is in the range of from about 2 to about 36 percent by weight. In many cases it is in the range of from about 3 to about 15 percent by weight. From about 3 to about 6 percent is preferred.

The feed composition usually, but not necessarily, contains small amounts of dissolved organic impurities in addition to the chloral. Examples of organic impurities which may also be present include 1,2-dichloroethane, monochloroacetaldehyde, dichloroacetaldehyde, ethanol, 2-chloroethanol, 1,2-dichloroethene, chloroform, and carbon tetrachloride. The concentration of such contaminants on a collective basis is usually less than about one-half of a percent by weight.

The feed composition may originate from substantially any source, but in most cases it has originated at least in part from the oxychlorination of ethylene.

The chloral concentration of the liquid reflux is in the range of from about 30 to about 89 percent by weight. Often the chloral concentration is in the range of from about 45 to about 89 percent by weight. A chloral concentration in the range of from about 65 to about 89 percent by weight is preferred.

The preceding discussion of ranges of chloral concentrations of the reflux is also applicable to ranges of chloral concentrations of the product. In most cases the composition of the product is the same as that of the reflux although if the product is withdrawn as a sidestream the compositions may differ.

The chloral concentration in the purified, aqueous hydrochloric acid solution is less than that in the feed composition. Usually the chloral concentration in the purified, aqueous hydrochloric acid solution is less than about 6000 parts per million by weight. In many cases the chloral concentration is less than about 500 parts per million by weight. Preferably the chloral concentration is less than about 50 parts per million by weight.

The concentration of hydrochloric acid, taken as HCl, present in the purified aqueous hydrochloric acid solution may be widely varied. Usually it is in the range from about 2 to about 20 percent by weight. Frequently the hydrochloric acid concentration, taken as HCl, is in the range of from about 3 to about 15 percent by weight. Preferably the hydrochloric acid concentration, taken as HCl, is in the range of from about 3 to about 6 percent by weight.

The pressure in the rectifying zone is superatmospheric. Usually the pressure in the rectifying zone is at least about 55 kilopascals gauge. Frequently the pressure is at least about 100 kilopascals gauge. In many cases the pressure in the rectifying zone is at least about 200 kilopascals gauge. Ordinarily the pressure in the rectifying zone is in the range of from about 55 to about 700 kilopascals gauge, while it is preferred that the pressure be in the range of from about 100 to about 520 kilopascals gauge. It is especially preferred that the pressure be in the range of from about 200 to about 450 kilopascals gauge.

The pressure in the stripping zone is also superatmospheric and usually it is at least about 55 kilopascals gauge. Frequently the pressure is at least about 100 kilopascals gauge. In many cases the pressure in the stripping zone is at least about 200 kilopascals gauge. Ordinarily the pressure in the stripping zone is in the range of from about 55 to about 700 kilopascals gauge, while preferably the pressure is in the range of from about 100 to about 520 kilopascals gauge. Pressures in the range of from about 200 to about 450 kilopascals gauge are particularly preferred.

The reflux ratio is in the range of from about 0.4:1 to about 15:1. In many cases the reflux ratio is in the range of from about 1:1 to about 10:1. A reflux ratio in the range of from about 3:1 to about 8:1 is preferred.

The recovered product has a wide variety of uses. For example, it may be used in the form in which it is recovered to produce other products such as trichloroacetic acid, 2,2,2-trichloroethanol, or chloroform. If desired, it may be further processed to recover the chloral.

Referring now in detail to the drawing, there is shown diagrammatically a reactor 1 in which ethylene is oxychlorinated to produce 1,2-dichloroethane. Ethylene from line 2 is admixed with hydrogen chloride from line 4 and the mixture passed through line 6 into reactor 1. Oxygen is passed through line 8 into reactor 1. The gaseous effluent from reactor 1 passes through line 10 to cooling system 12 where most of the effluent is condensed by coolant passing through line 13 to a liquid comprising an organic phase and an aqueous phase. The effluent is transferred through line 14 to phase separator 16 where the liquid phases are allowed to substantially separate into layers. Uncondensed gases may be removed through line 18. The lower liquid organic phase, which is a crude 1,2-dichloroethane composition, is removed through line 20 and may be processed to purify the 1,2-dichloroethane. The upper liquid aqueous phase, which is aqueous hydrochloric acid containing chloral and other organic contaminants, is removed through line 22 and introduced as feed to column 24 which contains packing material 26 and packing material 28, and which is maintained at superatmospheric pressure. The channels provided by packing material 26 constitute a stripping zone while the channels provided by packing material 28 constitute a rectifying zone. Steam is injected through line 30 into column 24 to provide vapor in the rectifying and stripping zones. If desired, a reboiler may be used either in lieu of or in addition to the steam injection. Within the channels provided by packing material 26 aqueous hydrochloric acid containing chloral is countercurrently contacted with reboiled aqueous acid vapors. A purified, aqueous hydrochloric acid solution having a lower concentration of chloral than the feed is recovered through line 34. Vapor from the rectifying zone is passed through line 36 and introduced to condenser 38 cooled by coolant passing through line 40. In condenser 38 most of the vapor is condensed to a liquid. Uncondensed gas may be removed through line 42. Liquid from condenser 38 is removed through line 44. A portion of the liquid passing through line 44 is introduced through line 46 to column 24 as reflux, while the remainder is recovered through line 48 as product. Both the reflux introduced to column 24 and the product comprise chloral and water in which the chloral concentration is in the range of from about 30 to about 89 percent by weight. Within the channels provided by packing material 26 aqueous hydrochloric acid containing chloral is countercurrently contacted with aqueous acid vapors. Within the channels provided by packing material 28 vapors comprising hydrochloric acid vapor and chloral vapor are countercurrently contacted with descending liquid comprising chloral and water.

For the sake of clarity in setting forth the nature of the system, parts of the apparatus such as valves, pumps, flow indicators, pressure indicators, pressure reducers, temperature indicators, hold-up tanks, storage tanks, and the like, not essential to a complete understanding of the invention have been omitted from the drawing.

It will be appreciated that various modifications can be made to the system of the drawing without departing from the spirit of the invention. For example, the column may be a bubble cap column, sieve plate column, or similar device. Single condensers may be replaced with a plurality of condensers operating in series and/or parallel. Other modifications will be apparent to those skilled in the art.

The invention is further described in conjunction with the following example, which is to be considered illustrative rather than limiting.

EXAMPLE

A column was constructed of 2.54 centimeter inside diameter borosilicate glass pipe that was packed with 1.829 meters of 6.35 millimeter Berl saddles. There were 1.524 meters of packing above the feed point and 0.305 meter below. The feed tank was a 4-liter graduated cylinder. The liquid from the feed tank flowed through 6.35 millimeter outside diameter polytetrafluoroethylene tubing to a variable flow pump that was fitted with a ceramic shaft and plastic head. (Unless otherwise noted, all tubing used in the construction of the apparatus was 6.35 millimeter outside diameter polytetrafluoroethylene tubing having a wall thickness of 1.1938 millimeter). After the pump, the feed entered a pre-heater constructed from 7.62 meters of coiled polytetrafluoroethylene tubing inside a 25.4 centimeter schedule 40 steel pipe that was 0.61 meter in length. Steam to the pre-heater was supplied from a 965 kilopascal gauge header and controlled by a regulator. The heated feed then entered the column.

Connected to the top of the column was a 2.54 centimeter borosilicate glass 90° elbow which was attached to the base of a 2.54 centimeter borosilicate glass tee. The straight run of the tee was oriented vertically so that the tee could be used as a reflux splitter. The lower opening of the tee was connected by a fitting to 6.35 millimeter tubing which was traced with electrical heating tape. The other end of this tubing was connected to a 9.525 millimeter orifice solenoid valve which was actuated by a timer. By adjusting the timer, the amount of overhead removed from the column could be controlled. The upper opening of the tee was connected by a fitting to 12.7 millimeter outside diameter polytetrafluoroethylene tubing having a wall thickness of 1.575 millimeters. The 12.7 millimeter tubing was continued to form a counter-current one-pass shell and tube condenser. The shell of the condenser was constructed of 2.54 centimeter chlorinated poly(vinyl chloride) pipe. Vapor from the column would flow up past the splitter, through the 12.7 millimeter polytetrafluoroethylene tubing, condense in the condenser, and return to the splitter through the same tubing. After passing through the condenser, the 12.7 millimeter tubing was connected by a fitting to 6.35 millimeter tubing that led to a control valve actuated by a pressure controller. This system regulated the pressure in the column. All of the 6.35 millimeter tubing in the overhead section of the system was traced with two sections of 12.7 millimeter wide electrical heating tape that were connected to the same variable autotransformer. Water, the temperature of which was estimated to be in the range of from about 45° C. to about 50° C., was introduced as a cooling medium on the shell side of the condenser. The temperature of the water leaving the shell side of the condenser was in the range of from 54° C. to 62° C.

Directly below the 2.54 centimeter borosilicate glass 90° elbow at the top of the column, nitrogen was introduced to the column through an opening provided for the purpose. The nitrogen provided a pad for smooth control of the column pressure while keeping corrosive fluid away from the stainless steel pressure transmitter. As a safety precaution, a 690 kilopascal rupture disc was connected to the system before the introduction of the nitrogen to provide pressure relief in the event of a control valve failure. The nitrogen was supplied by a cylinder controlled by a two stage regulator through a 6.35 millimeter manually operated needle valve.

A 2.54 centimeter borosilicate glass pipe cross was attached to the bottom of the column. One of the horizontal branches was used to remove bottoms from the system. This branch was connected by a fitting to polytetrafluoroethylene tubing that was coiled and submerged in an ice bath. After leaving the ice bath, the tubing was connected to the 6.35 millimeter branch of a 12.7 mm × 12.7 mm × 6.35 mm tee. Another branch of the tee was connected via 12.7 millimeter polytetrafluoroethylene tubing to the nitrogen line before the point of nitrogen introduction to the column. A liquid level sensor was mounted on the vertical portion of this tubing and set to the desired liquid level in the system. The remaining branch of the tee was connected via 12.7 millimeter polytetrafluoroethylene tubing to a manually operated valve that could be adjusted for smoother control of the liquid level in the system. This valve was connected via 12.7 millimeter polytetrafluoroethylene tubing to a 12.7 millimeter orifice polytetrafluoroethylene solenoid valve which was actuated by the liquid level sensor to allow liquid to leave the column as a bottoms stream. The bottoms stream then exited through two water cooled coolers that were arranged in parallel.

The lower vertical branch of the 2.54 centimeter borosilicate glass pipe cross was connected to a section of 2.54 centimeter diameter polytetrafluoroethylene-lined stainless steel braided hose that was 0.61 meter in length. The other end of this hose was connected to the offset branch of a borosilicate glass "Y" pipe. One straight run end of the "Y" pipe was connected to a 45° borosilicate glass elbow. This borosilicate glass elbow was connected to a horizontal branch of the cross to complete the reboiler loop. A quartz heater was inserted into the other straight run opening of the "Y" pipe and secured with a fitting. The hose was wrapped with two 1.83 meter lengths of electrical heating tape that were each 12.7 millimeters wide. The quartz heater and the heating tape were connected to separate variable autotransformers.

In operating the system, the reboiler was filled with water and the quartz heater and the heating tape around the hose were turned on. When the bottoms temperature reached approximately 60° C., the column was pressurized to 414 kilopascals gauge as measured at the top of the column. Initially tap water was fed to the column. When the overhead section of the column reached approximately 110° C., the timer was turned on to begin removing overhead from the column. The desired feed comprising hydrochloric acid and chloral was then introduced to the column. The flow rate of the overhead stream was adjusted and the run was started. The column was run for 1 to 2 hours before samples were removed to insure that the column was at steady state. At the end of the run the vapor traffic at the top of the column was measured. To measure this flow rate, the splitter was drained and no overhead was removed. The lower branch of the splitter tee was graduated to measure 6 milliliters of condensate. The length of time required to collect 6 milliliters of condensate was measured. From the time needed to collect 6 milliliters of the condensed vapor traffic, the density of this condensate, and the flow rate of the overhead stream, the reflux ratio was calculated. The data are shown in the Table.

TABLE

|  | Run 1 | Run 2 | Run 3 |
|---|---|---|---|
| Pressure, kPa gauge |  |  |  |
| Top of Column | 407 | 414 | 414 |
| Preheater | 441 | 538 | 496 |
| Temperature, °C. |  |  |  |
| Feed | 122 | 126 | 128 |
| Overhead | 135 | 131 | 129 |
| Bottoms | 151 | 152 | 150 |
| Mass Flow Rate, grams/hour |  |  |  |
| Feed | 1179 | 1179 | 907 |
| Overhead Product | 318 | 240 | 109 |
| Reflux | 141 | 227 | 481 |
| Reflux Ratio | 0.4 | 1.0 | 4.4 |
| Chloral Concentration, wt. percent |  |  |  |
| Feed | 10.9 | 9.4 | 10.1 |
| Overhead Product | 41.9 | 43.5 | 68.0 |
| Bottoms Product | 0.25 | 0.50 | 0.40 |
| Chloral Balance, percent | 97.3 | 96.0 | 91.3 |
| Overall Mass Balance, percent | 98.9 | 85.3 | 96.8 |
| Chloral Recovery, percent | 95.4 | 91.3 | 43.5 |

Although the present invention has been described with reference to specific details of certain embodiments thereof, it is not intended that such details should be regarded as limitations upon the scope of the invention except insofar as they are included in the accompanying claims.

We claim:
1. In the method wherein:
   (a) a feed composition comprising both aqueous hydrochloric acid and from about 1 to about 12 percent by weight chloral is introduced to a stripping zone;
   (b) aqueous hydrochloric acid containing chloral is countercurrently contacted in said stripping zone with steam or reboiled aqueous acid vapors under superatmospheric pressure conditions to produce a purified, aqueous hydrochloric acid solution having a lower concentration of chloral than said feed composition; and
   (c) at least a portion of said solution is recovered, the improvement comprising:
   (d) introducing liquid reflux to a rectifying zone at a reflux ratio of from about 0.4:1 to about 15:1, said liquid reflux comprising water and chloral in which the chloral concentration is in the range of from 30 to about 89 percent by weight;
   (e) countercurrently contacting in said rectifying zone under superatmospheric pressure conditions, vapors comprising hydrochloric acid vapor and chloral vapor with descending liquid comprising chloral and water; and
   (f) recovering a product comprising chloral and water in which the chloral concentration is in the range of from 30 to about 89 percent by weight.

2. The method of claim 1 wherein said superatmospheric pressure conditions in said rectifying zone are at least about 55 kilopascals gauge.

3. The method of claim 1 wherein said superatmospheric pressure conditions in said rectifying zone are in the range of from about 55 to about 700 kilopascals gauge.

4. The method of claim 1 wherein said superatmospheric pressure conditions in said rectifying zone are in the range of from about 200 to about 450 kilopascals gauge.

5. The method of claim 1 wherein said superatmospheric pressure conditions in said stripping zone are at least about 55 kilopascals gauge.

6. The method of claim 1 wherein said superatmospheric pressure conditions in said stripping zone are in the range of from about 55 to about 700 kilopascals gauge.

7. The method of claim 1 wherein the chloral concentration in said feed composition is in the range of from about 3 to about 10 percent by weight.

8. The method of claim 1 wherein the chloral concentration in said feed composition is in the range of from about 4 to about 6 percent by weight.

9. The method of claim 1 wherein the concentration of hydrochloric acid, taken as HCl, present in said feed composition is in the range of from about 2 to about 36 percent by weight.

10. The method of claim 1 wherein the chloral concentration of said liquid reflux is in the range of from about 45 to about 89 percent by weight and wherein the chloral concentration of said product is in the range of from about 45 to about 89 percent by weight.

11. The method of claim 1 wherein the chloral concentration of said reflux is in the range of from about 65 to about 89 percent by weight and wherein the chloral concentration of said product is in the range of from about 65 to about 89 percent by weight.

12. The method of claim 1 wherein said reflux ratio is in the range of from about 1:1 to about 10:1.

13. The method of claim 1 wherein said reflux ratio is in the range of from about 3:1 to about 8:1.

14. The method of claim 1 wherein the chloral concentration of said solution is less than about 6000 parts per million by weight.

15. The method of claim 1 wherein the chloral concentration of said solution is less than about 500 parts per million by weight.

16. The method of claim 1 wherein the chloral concentration of said solution is less than about 50 parts per million by weight.

17. The method of claim 1 wherein said rectifying zone and said stripping zone are contained in the same distillation column.

18. The method of claim 1 wherein said feed composition has originated at least in part from the oxychlorination of ethylene.

19. In the method wherein:
(a) a feed composition comprising both aqueous hydrochloric acid and from about 4 to about 6 percent by weight chloral is introduced to a stripping zone;
(b) aqueous hydrochloric acid containing chloral is countercurrently contacted in said stripping zone with steam or reboiled aqueous acid vapors under superatmospheric pressure conditions in the range of from about 200 to about 450 kilopascals gauge to produce a purified, aqueous hydrochloric acid solution in which the chloral concentration is less than about 50 parts per million by weight; and
(c) at least a portion of said solution is recovered, the improvement comprising:
(d) introducing liquid reflux to a rectifying zone at a reflux ratio of from about 1:1 to about 10:1, said liquid reflux comprising water and chloral in which the chloral concentration is in the range of from about 65 to about 89 percent by weight;
(e) countercurrently contacting in said rectifying zone under superatmospheric pressure conditions in the range of from about 200 to about 450 kilopascals gauge, vapors comprising hydrochloric acid vapor and chloral vapor with descending liquid comprising chloral and water; and
(f) recovering a product comprising chloral and water in which the chloral concentration is in the range of from about 65 to about 89 percent by weight.

20. The method of claim 19 wherein said feed composition has originated at least in part from the oxychlorination of ethylene.

21. The method of claim 19 wherein overhead vapor from said rectifying zone is introduced to a condenser where most of said overhead vapor is condensed to form a liquid condensate, a portion of said liquid condensate is introduced to said rectifying zone as said reflux, and the remainder of said liquid condensate is recovered as said product.

22. The method of claim 1 wherein overhead vapor from said rectifying zone is introduced to a condenser where most of said overhead vapor is condensed to form a liquid condensate, a portion of said liquid condensate is introduced to said rectifying zone as said reflux, and the remainder of said liquid condensate is recovered as said product.

* * * * *

UNITED STATES PATENT AND TRADEMARK OFFICE
CERTIFICATE OF CORRECTION

PATENT NO. : 4,628,122

DATED : Dec. 9, 1986

INVENTOR(S) : Kuntz et al.

It is certified that error appears in the above-identified patent and that said Letters Patent is hereby corrected as shown below:

On the Title Page:

In the References Cited section, Foreign Patent Documents, add the following foreign patent:

-- 49-83694   12/1972   Japan --

Signed and Sealed this

Fifteenth Day of December, 1987

Attest:

DONALD J. QUIGG

Attesting Officer

Commissioner of Patents and Trademarks